(12) United States Patent
Miller, II

(10) Patent No.: US 9,781,965 B2
(45) Date of Patent: Oct. 10, 2017

(54) WIRELESS MONITORING OF SAFETY HELMETS

(71) Applicant: AT&T Intellectual Property I, L.P., Atlanta, GA (US)

(72) Inventor: Robert R. Miller, II, Convent Stn., NJ (US)

(73) Assignee: AT&T INTELLECTUAL PROPERTY I, L.P., Atlanta, GA (US)

( * ) Notice: Subject to any disclaimer, the term of this patent is extended or adjusted under 35 U.S.C. 154(b) by 0 days.

(21) Appl. No.: 15/215,989

(22) Filed: Jul. 21, 2016

(65) Prior Publication Data

US 2017/0006950 A1 Jan. 12, 2017

Related U.S. Application Data

(63) Continuation of application No. 14/691,162, filed on Apr. 20, 2015, now Pat. No. 9,420,840, which is a (Continued)

(51) Int. Cl.
*G08B 23/00* (2006.01)
*A42B 3/04* (2006.01)
(Continued)

(52) U.S. Cl.
CPC ............ *A42B 3/046* (2013.01); *A61B 5/0004* (2013.01); *A61B 5/0022* (2013.01); *A61B 5/11* (2013.01); *A61B 5/1122* (2013.01); *A61B 5/4064* (2013.01); *A61B 5/6803* (2013.01); *A61B 5/6898* (2013.01); *A61B 5/7246* (2013.01); *A61B 5/7264* (2013.01); *A61B 5/7282* (2013.01); *A61B 5/742* (2013.01); *A61B 5/746* (2013.01); *A61B 5/747* (2013.01); *G08B 21/043* (2013.01); *A61B 2562/028* (2013.01); *A61B 2562/0219* (2013.01);
(Continued)

(58) Field of Classification Search
CPC combination set(s) only.
See application file for complete search history.

(56) References Cited

U.S. PATENT DOCUMENTS 3,645,259 A   2/1972   Schulman
3,668,526 A   6/1972   Raskin
(Continued)

OTHER PUBLICATIONS

Office Action dated Oct. 9, 2012 for U.S. Appl. No. 13/010,353, 36 pages.
(Continued)

*Primary Examiner* — Travis Hunnings
(74) *Attorney, Agent, or Firm* — Amin, Turocy & Watson, LLP

(57) ABSTRACT

Remote monitoring of a subject wearing a sports helmet is enabled. In one aspect, an example system includes a safety helmet and a sensor integrated with the helmet for continuously gathering head acceleration force data, the head acceleration force data associated with the head movements of a subject. The system can also include a wireless transceiver coupled to the sensor for transmitting the head acceleration force data and a mobile device for receiving the head acceleration force data from the wireless transceiver. The system can further include a database engine for displaying the head acceleration force data to a user.

20 Claims, 13 Drawing Sheets

Related U.S. Application Data continuation of application No. 13/010,353, filed on Jan. 20, 2011, now Pat. No. 9,035,776.

(51) Int. Cl.
  *G08B 21/04* (2006.01)
  *A61B 5/00* (2006.01)
  *A61B 5/11* (2006.01)

(52) U.S. Cl.
  CPC ... *A61B 2562/0247* (2013.01); *A61B 2562/04* (2013.01); *A61B 2562/043* (2013.01)

(56) References Cited

U.S. PATENT DOCUMENTS

| | | | |
|---|---|---|---|
| 3,936,822 A | 2/1976 | Hirschberg | |
| 4,477,041 A | 10/1984 | Dunne | |
| 4,688,037 A | 8/1987 | Krieg | |
| 4,903,346 A | 2/1990 | Reddemann et al. | |
| 5,039,035 A | 8/1991 | Fitzpatrick | |
| 5,200,736 A | 4/1993 | Coombs et al. | |
| 5,208,514 A | 5/1993 | Bassick | |
| 5,272,770 A | 12/1993 | Allen et al. | |
| 5,322,245 A | 6/1994 | Bassick | |
| 5,329,637 A | 7/1994 | Walker | |
| 5,539,935 A | 7/1996 | Rush | |
| 5,621,922 A | 4/1997 | Rush | |
| 5,978,972 A | 11/1999 | Stewart et al. | |
| 6,826,509 B2 * | 11/2004 | Crisco, III | 2/422 |
| 7,091,875 B2 | 8/2006 | Ondracek | |
| 7,519,405 B1 | 4/2009 | Brent | |
| 7,747,559 B2 | 6/2010 | Leitner et al. | |
| 7,930,771 B2 | 4/2011 | Depreitere et al. | |
| 7,941,873 B2 | 5/2011 | Nagely et al. | |
| 7,992,421 B2 | 8/2011 | Jeftic-Stojanovski et al. | |
| 8,181,281 B2 | 5/2012 | Nagely et al. | |
| 8,232,881 B2 | 7/2012 | Hertz | |
| 9,035,776 B2 * | 5/2015 | Miller, II | A42B 3/046 340/10.1 |
| 9,420,840 B2 * | 8/2016 | Miller, II | A42B 3/046 |
| 2002/0070881 A1 | 6/2002 | Marcarelli et al. | |
| 2002/0160723 A1 | 10/2002 | Yagi | |
| 2003/0197608 A1 | 10/2003 | Rudhard | |
| 2005/0086579 A1 | 4/2005 | Leitner et al. | |
| 2005/0162265 A1 | 7/2005 | Werner et al. | |
| 2006/0038694 A1 | 2/2006 | Naunheim et al. | |
| 2006/0062376 A1 | 3/2006 | Pickford | |
| 2006/0071781 A1 | 4/2006 | Ondracek | |
| 2006/0074338 A1 * | 4/2006 | Greenwald | A61B 5/0002 600/549 |
| 2007/0061041 A1 | 3/2007 | Zweig | |
| 2007/0089480 A1 | 4/2007 | Beck | |
| 2007/0245465 A1 | 10/2007 | Neal et al. | |
| 2008/0066217 A1 | 3/2008 | Depreitere et al. | |
| 2008/0256687 A1 | 10/2008 | Spencer | |
| 2009/0045285 A1 | 2/2009 | Mastrolia | |
| 2010/0005571 A1 | 1/2010 | Moss et al. | |
| 2010/0095439 A1 | 4/2010 | Nolan et al. | |
| 2010/0102970 A1 | 4/2010 | Hertz | |
| 2010/0155535 A1 | 6/2010 | Mastrolia | |
| 2010/0170022 A1 | 7/2010 | Griffiths | |
| 2010/0298683 A1 | 11/2010 | Cabrera et al. | |
| 2010/0307223 A1 | 12/2010 | Jeftic-Stojanovski et al. | |
| 2011/0084167 A1 | 4/2011 | Mastrolia | |
| 2011/0150206 A1 | 6/2011 | Pickford | |
| 2011/0184663 A1 * | 7/2011 | Mack | A42B 3/046 702/41 |
| 2011/0185481 A1 | 8/2011 | Nagely et al. | |
| 2011/0204891 A1 | 8/2011 | Drake et al. | |
| 2011/0215931 A1 * | 9/2011 | Callsen | F41H 1/04 340/573.1 |
| 2011/0218756 A1 * | 9/2011 | Callsen | F41H 1/04 702/139 |
| 2011/0218757 A1 | 9/2011 | Callsen et al. | |
| 2011/0219852 A1 | 9/2011 | Kasten | |
| 2012/0036620 A1 | 2/2012 | Harris | |
| 2012/0092178 A1 | 4/2012 | Callsen et al. | |
| 2012/0147009 A1 | 6/2012 | Benzel et al. | |
| 2012/0222197 A1 | 9/2012 | Nagely et al. | |
| 2013/0042861 A1 | 2/2013 | Baek | |

OTHER PUBLICATIONS

Office Action dated Jan. 31, 2013 for U.S. Appl. No. 13/010,353, 46 pages.
Office Action dated Mar. 21, 2015 for U.S. Appl. No. 13/010,353, 64 pages.
Office Action dated Aug. 13, 2014 for U.S. Appl. No. 13/010,353, 87 pages.
Office Action dated Dec. 8, 2015 for U.S. Appl. No. 14/691,162, 21 pages.

* cited by examiner

WIRELESS MONITORING OF SAFETY HELMETS

CROSS REFERENCE

This patent application is a continuation of, and claims priority to, U.S. patent application Ser. No. 14/691,162, filed on Apr. 20, 2015, and entitled "WIRELESS MONITORING OF SAFETY HELMETS", which is a continuation of, and claims priority to, U.S. patent application Ser. No. 13/010,353, filed on Jan. 20, 2011, and entitled "WIRELESS MONITORING OF SAFETY HELMETS" (now U.S. Pat. No. 9,035,776). The entireties of the aforementioned applications are hereby incorporated by reference herein.

TECHNICAL FIELD

This disclosure relates generally to wireless monitoring of safety helmets.

BACKGROUND

Personal alarm systems are well known in the art. Some of these systems are used to maintain surveillance of children. They may also be used to monitor the safety of employees involved in dangerous work at remote locations or to monitor the safety of physically or mentally handicapped people. They may even be used to find lost or stolen vehicles and strayed pets.

Every year, thousands of children and adults suffer injuries during various recreational and athletic activities. These injuries occur mostly during recreational activities, although injuries can also occur during training or during various national and international competitions. For example, one of the most frequently occurring injuries in gymnastics is due to falls or improper landing after dismount from the parallel bars, high bars or rings. Most injuries occur during practice, even though in these situations mats with various thickness and degree of softness, depending on the characteristics of the gymnast and his/her degree of expertise and the type of exercise to be performed, are commonly placed in the landing area to absorb the shock during landing or in case of a fall. The most dangerous fall is where an athlete falls on his/her head. Such falls can cause serious spinal injury and may even be fatal. Falls on the shoulder, side or the back are less dangerous, but may cause serious soft tissue damage and/or bone fracture or joint dislocation. Uncontrollable foot landing is usually least dangerous, with the most probable short-term injuries being those of the knee or ankle due to twisting of the foot and/or the knee joints. However, with the current mats in use, particularly with the stiffer mats used while practicing dismount and landing and in competitions, the high level of repetitive impact loading of the limbs, particularly the foot, ankle and the knee joints, and even the spinal structure can cause serious long-term medical problems.

Additionally, the increasing awareness of head injuries has also become more widely known in recent years. Although helmets are worn, especially by young children, during many of these activities, helmets do not always protect against all of the different head traumas, especially injuries associated with rapid acceleration of the helmet wearer's head.

Existing monitoring systems use radio technology to link a remote transmitting unit with a base receiving and monitoring station. The remote unit is usually equipped with one or more hazard sensors and is worn or attached to the person or thing to be monitored. When a hazard is detected, the remote unit transmits to the receiving base station where an operator can take appropriate action in responding to the hazard.

The use of personal alarm systems to monitor the activities of children has become increasingly popular. A caretaker attaches a small remote unit, no larger than a personal pager, to an outer garment of a small child. If the child wanders off or is confronted with a detectable hazard, the caretaker is immediately notified and can come to the child's aid. In at least one interesting application, a remote unit includes a receiver and an audible alarm which can be activated by a small hand-held transmitter. The alarm is attached to a small child. If the child wanders away in a large crowd, such as in a department store, the caretaker actives the audible alarm which then emits a sequence of "beeps" useful in locating the child in the same way one finds a car at a parking lot through the use of an auto alarm system.

There is a trade-off between constant monitoring of children's activities and the risk of injuries or endangerment to the welfare of the children. Childhood activities like biking, skateboarding, horseback riding, and skiing, for example, are formative for physical development and competitive spirit, however they carry some risk of injury, particularly head injuries. The CDC reported that in 2008 there were more than a quarter of a million bicycle injuries for children 19 or younger with most injuries in the 5-14 year range. Thus, helmets are required or strongly encouraged when participating in such activities. Moreover, children benefit in terms of independence and self-reliance when forming groups with others of the same age. Hence, there is a need to encourage children to engage in unsupervised activities, while also enabling immediate response in the event of an accident or emergency.

BRIEF DESCRIPTION OF THE DRAWINGS

Various non-limiting embodiments are further described with reference to the accompanying drawings in which.

DETAILED DESCRIPTION

Overview

Figure 1:
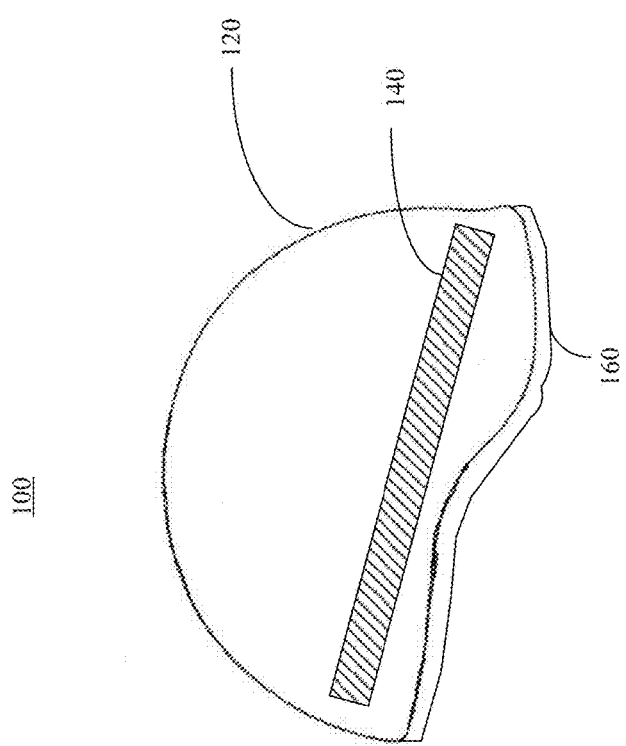
FIG. 1 is a simplified schematic illustrating a safety helmet according to exemplary embodiments.

Today, most children wear helmets when biking and also carry a cell phone. Hence, in accordance with the disclosed subject matter, parents or caregivers can virtually "watch at a distance", and in particular be alerted immediately in the event of an accident.

Considering the importance of child safety, there are many systems aimed at child safety, such as what are known as toddler telemetry systems. However, there remains room for improvement with these systems. One such area for improvement relates to increasing the useful life of a battery used to power the remote unit of these toddler telemetry systems.

Another room for improvement in the area of children's safety remains the risk of head injuries. It is known that the human body's ability to tolerate increases in cranial pressure above the static pressure depends on (1) the rate of pressure increase; (2) the peak value (i.e., magnitude) of the pressure increase; and (3) the duration of the pressure increase. In general, slow increases in pressure are tolerated well, even for long durations. However, serious injury can occur when the pressure rises rapidly (microseconds or less), as in an accident. The sudden increase (rapid rise time) in pressure that exceeds the static pressure, especially one that is induced by an accident, is called overpressure. The pressure eventually returns to the static value long after the accident has passed.

In general, the greater the magnitude of the overpressure and the longer the duration of the overpressure, the more severe the biological damage due to the accident. One common form of measuring the rapid acceleration or deceleration of a subject is "G's" which is defined as a unit of acceleration equal to the acceleration of gravity at the earth's surface. For example, a few G's experienced for a few milliseconds is known to cause severe biological damage. The severity of the problem is compounded because simulations have shown that even small overpressures with rapid rise times can produce significant flexure in the skull which can generate large pressure gradients in the brain. The present disclosure addresses this and other problems.

Additionally, the use of wireless communication devices have become so prevalent in today's society that almost everyone uses a cell phone or other wireless communication device for communication with one another. As people become more confident with the use of these wireless communication devices and the services they provide, the use of wired devices, such as a wired telephone at home, have become less important in day-to-day life. The result of this change in behavior has led many people to discontinue their wired communication service and rely entirely on their wireless communication device. In some circumstances, such as those living on the fringe of service or living in large multi-unit complexes, the marginal signal strength in these locations makes relying entirely on a wireless service a somewhat risky proposition.

The above-described deficiencies of today's safety monitoring of children while the children are engaged in various activities are merely intended to provide an overview of some of the problems of conventional systems, and are not intended to be exhaustive. Other problems with the state of the art and corresponding benefits of one or more of the various non-limiting embodiments may become further apparent upon review of the following detailed description.

The disclosure describes embodiments for monitoring and tracking the use of safety helmets. In one aspect, such embodiments can include a system for remote tracking of head injuries, comprising: a safety helmet; at least one sensor integrated with the safety helmet for substantially continuously gathering head acceleration force data, the head acceleration force data associated with the head movements of a subject; a wireless transceiver coupled to the at least one sensor for transmitting the head acceleration force data; a mobile device for receiving the head acceleration force data from the wireless transceiver; and a database engine for displaying the head acceleration force data to a user's sports activities.

In another aspect, such embodiments can include a method for monitoring sports activities, comprising: continuously gathering biometric data from a subject performing a sports activity, the biometric data associated with the body movements of the subject; transmitting the biometric data at a transceiver; receiving the biometric data at a database engine; and providing real-time feedback associated with the biometric data from the subject, the real-time feedback characterized by instructions associated with the sports activity.

In yet another aspect, such embodiments can include a method for remote tracking of head injuries, comprising: substantially continuously gathering head acceleration force data at a sensor, the sensor integrated with a safety helmet; transmitting the head acceleration force data at a transceiver to a database engine; receiving the head acceleration force data at a mobile device; and providing real-time feedback associated with the head acceleration force data from the subject from a database engine integrated with the mobile device.

In one aspect, such embodiments can include a system for wireless monitoring of safety helmets worn by children, comprising: a database engine for receiving head acceleration force data from a wireless transceiver and providing real-time feedback, wherein the database engine is coupled to a wireless transceiver via at least one wireless communication network, and wherein the wireless transceiver is coupled to at least one sensor for substantially continuously gathering the head acceleration force data from a child; wherein the real-time feedback associated with the head acceleration force data from the child, and wherein if the head acceleration force data exceeds a threshold, the data is displayed at a mobile device associated with the database engine.

Remote Tracking of Head Injuries

One or more embodiments are now described with reference to the drawings, wherein like reference numerals are used to refer to like elements throughout. In the following description, for purposes of explanation, numerous specific details are set forth in order to provide a thorough understanding of the various embodiments. It may be evident, however, that the various embodiments can be practiced without these specific details, e.g., without applying to any particular networked environment or standard. In other instances, well-known structures and devices are shown in block diagram form in order to facilitate describing the embodiments in additional detail.

As used in this application, the terms "component," "module," "system," "engine," "interface," "platform," "station," "framework," "connector," or the like are generally intended to refer to a computer-related entity, either hardware, a combination of hardware and software, software, or software in execution or an entity related to an operational machine with one or more specific functionalities. For example, a component may be, but is not limited to being, a process running on a processor, a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers. As another example, an interface can include I/O components as well as associated processor, application, and/or API components.

Further, the various embodiments can be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, carrier, or media. For example, computer readable media can include but are not limited to magnetic storage devices (e.g., hard disk, floppy disk, magnetic strips . . . ), optical disks (e.g., compact disk (CD), digital versatile disk (DVD) . . . ), smart cards, and flash memory devices (e.g., card, stick, key drive . . . ). Additionally it should be appreciated that a carrier wave can be employed to carry computer-readable electronic data such as those used in transmitting and receiving electronic mail or in accessing a network such as the Internet or a local area network (LAN). Of course, those skilled in the art will recognize many modifications can be made to this configuration without departing from the scope or spirit of the various embodiments.

In addition, the words "exemplary" and "example" are used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Moreover, terms like "user equipment," "mobile station," "mobile," subscriber station," "access terminal," "terminal," "handset," "end device," "mobile device," and similar terminology, refer to a wireless device utilized by a subscriber or user of a wireless communication service to receive or convey data, control, voice, video, sound, gaming, or substantially any data-stream or signaling-stream. The foregoing terms are utilized interchangeably in the subject specification and related drawings. Likewise, the terms "base station," "Node B," "evolved Node B," "home Node B (HNB)," and the like, are utilized interchangeably in the subject application, and refer to a wireless network component or appliance that serves and receives data, control, voice, video, sound, gaming, or substantially any data-stream or signaling-stream from a set of subscriber stations. Data and signaling streams can be packetized or frame-based flows.

Furthermore, the terms "child," "children," "parent," "caregiver," "user," "subscriber," "customer," and the like are employed interchangeably throughout the subject specification, unless context warrants particular distinction(s) among the terms. It should be appreciated that such terms can refer to human entities or automated components supported through artificial intelligence (e.g., a capacity to make inference based on complex mathematical formalisms), which can provide simulated vision, sound recognition and so forth. In addition, terms "core network", "core mobility network", "service provider network" and the like are employed interchangeably throughout the subject specification, unless context warrants particular distinction(s) among the terms.

The disclosure is generally directed to child monitor systems in which sensor data is transmitted or sensor data is stored for later transmission in a "store and forward" scheme so that captured sensor data can be monitored and analyzed, distributed, or for other uses. In some cases, the sensor data is stored in response to a remote request for storage of the captured content made from a parent unit. Issuing an instruction to store the content data remotely allows a caregiver to assess whether the content should be recorded without disturbing or distracting the child. The devices and systems described herein generally support and provide such remote content capture and data storage, as well as the subsequent distribution, viewing, sharing, and other uses. In these ways, the caregiver can monitor the candid and uninfluenced content reproduced from a real-time data stream or feed, and at any time initiate data storage of a selected portion of the corresponding content data.

Some aspects of the disclosure are directed to overcoming challenges introduced by the portable nature of the parent unit used to monitor the content. At the outset, a portable parent unit is more convenient than stationary monitors associated with webcam-based or other remotely controlled video camera systems. The caregiver avoids being inconveniently tied to the location of a computer or other terminal. However, the maintenance of the wireless communication link can be complicated by the repositioning of the parent unit. Therefore, some aspects described below may adjust operational parameters or transmission characteristics to accommodate the varying, wireless nature of the communication link, while still supporting the transmission of the content data to be stored. In these ways, the content is recorded at a quality level (e.g., resolution) appropriate for reproduction via devices other than the small display of the parent unit.

Some aspects of the disclosure are directed to facilitating the capture of content that is fleeting or difficult to anticipate or predict. For instance, some aspects may utilize a buffer configured to store the content data in a continuous manner. A user request to store recently displayed content then relies on the storage capacity of the buffer to store data representative of past content, as further described below.

Some aspects of the disclosure are directed to addressing the challenges of supporting continuous, real-time, wireless broadcasts of the captured content in connection with the monitoring function, while recording on-demand high-quality images or other content for subsequent enjoyment. In past systems, the quality of the content as displayed on the parent unit can be inadequate or otherwise undesirable when not viewed in real-time. Using the devices, systems and techniques disclosed herein, caregivers can use the real-time broadcast to assess the content, and then select a portion thereof for storage at a high resolution or quality level.

Although described in connection with exemplary child monitor systems involving the capture of audio or image data for a caregiver, the disclosed techniques, devices and systems are well suited for implementation and use in a variety of contexts and applications. Practice of the disclosed techniques, devices and systems is accordingly not limited to a particular child monitoring context or application. For instance, although described in connection with portable parent units, several aspects of the disclosure are equally applicable to non-portable units. The systems are also not limited to video monitors or monitors having cameras, and are instead well suited for any type of content or content sensor, including those systems that may be user-configurable or otherwise switch between content types or combinations thereof.

Turning now to FIG. 1, there is illustrated a view of a child protective helmet 100, according to an aspect of the current innovation. The protective helmet 100 includes an outer shell 120 defined by a crown portion that is integrally formed with a brim 160. Head gear (not shown) that is configured to be adjustably positioned around a wearer's head may be coupled to, and positioned underneath and/or within, the crown portion so that the wearer may comfortably and securely wear the protective helmet 100. The protective helmet 100 may be any type of protective helmet, including a biking helmet, a helmet used in sports such as baseball, hockey, football, lacrosse, bobsledding, a military, construction-worker, or fireman's helmet, or various other types of helmets used to protect the head of a wearer.

The protective helmet 100 may be formed from a standard polyethylene or polycarbonate base with a phosphorescent material coating the base. Optionally, the protective helmet 100 may be formed from polyetherimide, polyamide, polypropylene, Acrylonitrile-butadine-styrene (ABS), polyurethane, polystyrene, or the like.

For example, the outer shell 120 may be formed through a polyethylene or polycarbonate molding process. After the outer shell 120 is formed, a layer of phosphorescent material may be formed over the outer shell 120. Alternatively, the molding process for the outer shell 120 may include forming the outer shell from a standard polymer material mixed with a phosphorescent material. Further, the outer shell 120 may be formed from a standard polymer material after which, phosphorescent strips, or the like, are fastened to the outer surface of the outer shell 120. In other words, the entire outer shell 120 may include phosphorescent material, or, optionally, phosphorescent material may cover only portions of the outer shell 120. The phosphorescent material may be, or include, high performance rare earth (lanthanide) doped strontium aluminate and/or strontium silicate crystals. These crystals may first be compounded into a high density polyolefin polymer such as (but not limited to) high density polyethylene or polycarbonate, to which one or more specialty lubricants are added In one or more aspect, the helmet 100 also includes one or more sensors 140 shown as being disposed inside the inner lining of the helmet 100. It will be understood that the sensors may be alternatively disposed along the brim 160 or at the top of the crown point of the helmet 100. In another aspect, the sensors may be disposed externally on the helmet 100. In one or more aspect, the sensors 140 may be disposed externally on the outer surface of the helmet.

In one or more aspect, the sensor 140 is a pressure sensitive array of sensors. A large-enough force triggers the helmet 100 to provide a measurement of vector accelerations experienced by the combination of the helmet 100 and the head. The companion pressure-sensitive array measures actual force applied to the head in various areas, which along with the acceleration and pressure time waveform represents the best current determination of whether injury may have occurred and how severe the injury might be.

In another aspect, the sensors 140 are comprised of a time of arrival (TOA) gauge sensors that produces a TOA signal in response to a positive pressure change above a predetermined threshold pressure. The positive pressure change TOA signals are sent to a receiver (not shown) to be stored, processed, and/or transmitted to a remote location. In a preferred aspect, four or more external sensors, each with a positive-pressure-change TOA gauge, are used and spaced from each other and positioned externally on the helmet.

The sensor 140 measures the presence, velocity, directionality, and magnitude (peak pressure) of the wearer's head. Typically, three external sensors are required to determine a plane of motion of the head (i.e., directionality), and a fourth sensor to determine the velocity and magnitude of the peak pressure. In one aspect, the positive-pressure-change gauges responds only to positive pressure above a certain threshold pressure. In another aspect, the threshold pressure may be chosen to neglect pressure changes due to weather or altitude.

Figure 2:
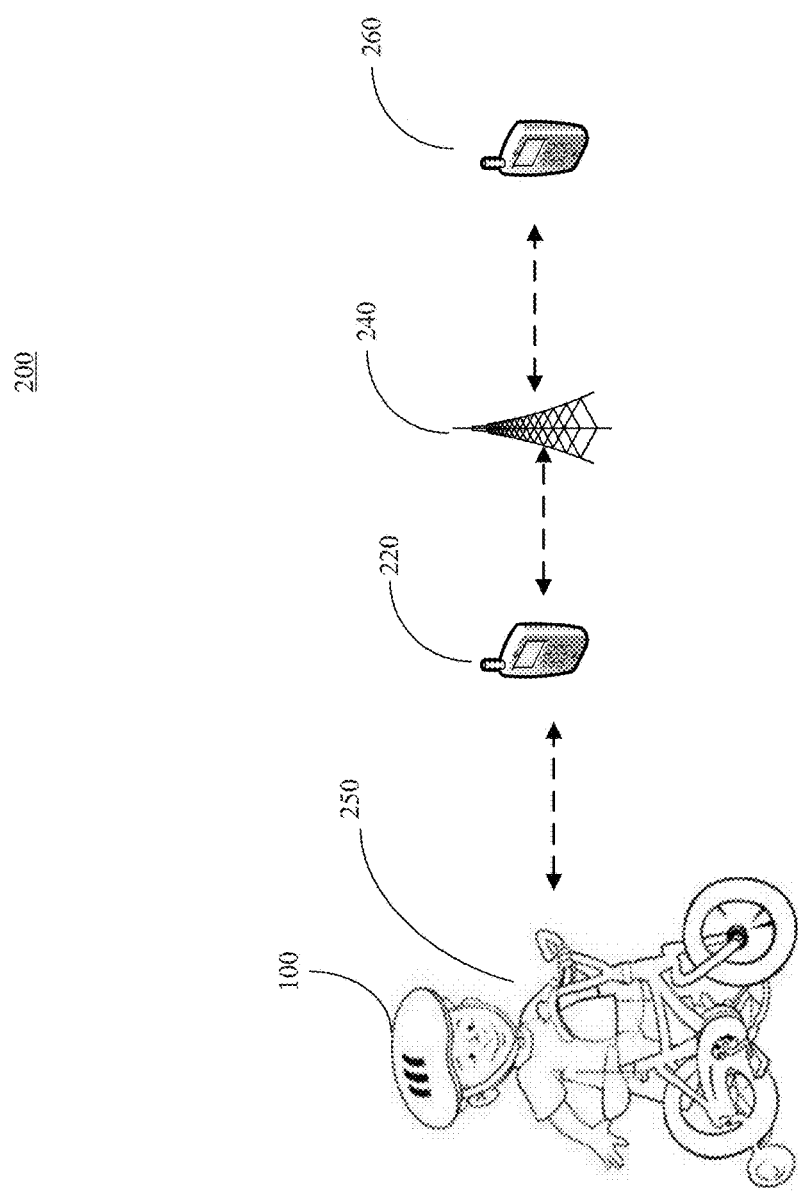
FIG. 2 is a simplified schematic illustrating an operating environment according to exemplary embodiments.

Turning now to FIG. 2, there is depicted an exemplary child monitor system indicated generally as 200. The subject 250 is depicted as a child with a bicycle. It will be understood that the subject 250 may be a child engaged in various other activities such as skiing, snowboarding, baseball, softball, football, hockey, or simply playing in a playground. Although the subject 250 is depicted with just a helmet 100 with the pressure sensor (e.g., sensor 140) integrated therein, the subject 250 may have various other biometric and biomechanical sensors positioned on the subject's body.

For example, the sensors may be attached to the subject's clothing or shoes or may be woven or positioned with the subject's clothing or shoes. In one aspect, the sensors can be associated with joints and appendages of the body in order to track position and or movement of such joints and appendages. The sensors can gather data relating to various physical characteristics, positions, changes, performance, or properties of the subject. This data can be referred to as "biometric" data. Biometric data includes biomedical and biomechanical data, and can include any of the following: data tracing the trajectory, speed, acceleration, position, orientation, etc. of a subject's appendage or other body part; data showing the heart rate, blood pressure, temperature, stress level, moisture content, toxin level, viability, respiration rate, etc. of a subject; data showing whether or not a subject is performing a signal or communication movement (e.g., teeth closed, arm cocked, etc.); data showing the posture or other status of a subject (e.g., prone or erect, breathing or not, moving or not); data showing the emotional state of a subject; etc.

For example, the sensors can track movement of the subject and/or tension in the subject's muscles. In some embodiments, the sensors can include one or more of the following technologies: accelerometer technology that detects accelerations; gyroscope technology that detects changes in orientation; compass or magnetic technology that senses position and/or alignment with relation to magnetic fields; satellite-based, global positioning satellite (GPS)-style technology; radio-frequency technology; etc. In this regard, any location module can be employed. In some aspects, sensors can be embedded in the skin of a user. The sensors can gather data relating to the subject's form, balance, gait, speed, position, and/or stride. The sensors can then send data to a transceiver (not shown).

The transceiver may have a clip for attaching to a belt, for example. The clip can rotate in order to allow the transceiver to be oriented in various ways, according to the needs or the whim of the child. The transceiver may be connected to the various sensors by wires or leads (not shown). In a preferred aspect, the transceiver can gather data from the various sensors by a wireless connection. In some aspects, the data is transmitted wirelessly (using radio frequency transmissions, for example). Various communications protocols can be used, including, for example, Bluetooth, ZigBee, TCP/IP, 802.11b, 802.11a, 802.11g, 802.11e, etc.).

The transceiver forwards the data wirelessly to a mobile device 220. In some aspects, the transceiver can transmit data wirelessly via the internet. In another aspect, the transceiver can store data on its onboard memory (or a memory card) for later transfer to the mobile device. In a preferred aspect, the transceiver is a mobile device, a cell phone, smartphone, personal digital assistant (PDA), pocket PC, tablet PC, MP3 player, or other portable communications and/or computing device. The mobile device may be a disposable cell phone or a prepaid cell phone. In some aspects, the transceiver can send signals to and/or receive signals from a portable communications device such as those mentioned here, for example.

The data is gathered at the mobile device 220. In one aspect, appropriate software on the mobile device 220 analyzes the data and may provide a graphical evaluation of the pressure data derived from sensors associated with the child or subject 250. The graphical evaluation may include, but is not limited to, the pressure data being shown with graphs, numbers, graphical depictions, charts, histograms, etc. The performance evaluation can include statistical analyses that, for example, determine the subject's average pressure data and the subject's deviations from this average. For example, statistical techniques can be used to compare the subject's pressure change data with other suitable subjects as defined by demographics, geography, performance level, etc.

In one aspect, a threshold may be customizable by the parent or guardian of the subject 250 so that only pressure change events which exceed a predefined threshold is recorded or stored at the mobile device 220. Any pressure change events which exceed the predefined threshold can be transmitted from the mobile device 220 through the wireless network 240 to a second mobile device 260. This data transmission may occur through the wireless network 240 or some other suitable network. It will be understood that, in some aspects, the second mobile device 260 may be a cell phone, smartphone, personal digital assistant (PDA), pocket PC, tablet PC, MP3 player, or other portable communications and/or computing device and may supplement, or in some cases, be used in lieu of the mobile device 260 described herein.

For example, a cell phone, PDA, etc. can upload data to the World Wide Web, and that data (in raw or processed form) can also be accessed from the cell phone, PDA, etc. In some aspects, a user's data can be sent to a "learning center" or suitable web server via the World Wide Web, and then that same user can thereafter access charts, histograms, etc. that are visible on that user's cell phone, PDA, etc. that provide insight to the user relating to the data and/or the user's performance.

The mobile device 220 transmits data to a first processor. The data can be transmitted in electronic or electromagnetic form, for example. In some aspects, the data is transmitted wirelessly (using radio frequency transmissions, for example). Various communications protocols can be used, including, for example, Bluetooth, ZigBee, TCP/IP, 802.11b, 802.11a, 802.11g, 802.11e, etc.). In some aspects, the transceiver transmits the data over the internet or over a wired or wireless network.

Figure 3:
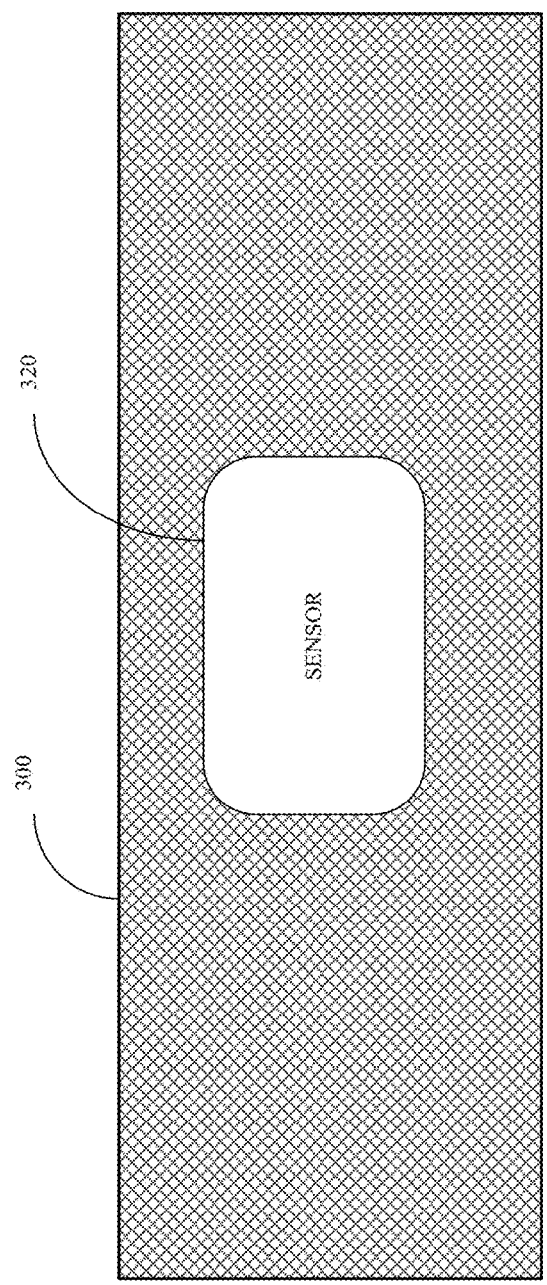
FIG. 3 is a simplified schematic illustrating an operating environment according to exemplary embodiments.

Referring now to FIG. 3, there is shown a sensor arrangement 300 in accordance with an exemplary embodiment of the subject innovation. Sensor 320 can be woven into the inner lining of a helmet. In another aspect, the sensor 320 can be incorporated into the outer shell defined by a crown portion that is integrally formed with a brim. Head gear (not shown) that is configured to be adjustably positioned around a wearer's head may be coupled to, and positioned underneath and/or within, the crown portion so that the wearer may comfortably and securely wear the protective helmet. The protective helmet may be any type of protective helmet, including a biking helmet, a helmet used in sports such as baseball, hockey, football, lacrosse, bobsledding, a fireman's helmet, or various other types of helmets used to protect the head of a wearer.

The protective helmet may be formed from a standard polyethylene or polycarbonate base with a phosphorescent material coating the base. Optionally, the protective helmet may be formed from polyetherimide, polyamide, polypropylene, Acrylonitrile-butadine-styrene (ABS), polyurethane, polystyrene, and the like.

For example, the outer shell may be formed through a polyethylene or polycarbonate molding process. After the outer shell is formed, a layer of phosphorescent material may be formed over the outer shell. Alternatively, the molding process for the outer shell may include forming the outer shell from a standard polymer material mixed with a phosphorescent material. Further, the outer shell may be formed from a standard polymer material after which, phosphorescent strips, or the like, are fastened to the outer surface of the outer shell. In other words, the entire outer shell may include phosphorescent material, or, optionally, phosphorescent material may cover only portions of the outer shell. The phosphorescent material may be, or include, high performance rare earth (lanthanide) doped strontium aluminate and/or strontium silicate crystals. These crystals may first be compounded into a high density polyolefin polymer such as (but not limited to) high density polyethylene or polycarbonate, to which one or more specialty lubricants are added In one aspect, the helmet also includes one or more sensors shown as being disposed inside the inner lining of the helmet. It will be understood that the sensors may be alternatively disposed along the brim or at the top of the crown point of the helmet. In another aspect, the sensors may be disposed externally on the helmet. In one aspect, the sensors may be disposed externally on the outer surface of the helmet.

In one aspect, the sensor is a pressure sensitive array of sensors. The pressure sensitive array is a microelectromechanical system (MEMS) 3-axis accelerometer and pressure sensor array along with a ZigBee radio and battery. A large enough force triggers the helmet to provide a measurement of vector accelerations experienced by the combination of the helmet and the head. The companion pressure-sensitive array measures actual force applied to the head in various areas, which along with the acceleration and pressure time waveform represents the best current determination of whether injury may have occurred and how severe the injury might be.

In another aspect, the sensors are comprised of a time of arrival (TOA) gauge sensors that produces a TOA signal in response to a positive pressure change above a predetermined threshold pressure. The positive pressure change TOA signals are sent to a receiver (not shown) to be stored, processed, and/or transmitted to a remote location. In a preferred aspect, four or more external sensors, each with a positive-pressure-change TOA gauge, are used and spaced from each other and positioned externally on the helmet.

The sensor measures the presence, velocity, directionality, and magnitude (peak pressure) of the wearer's head. Typically, three external sensors are required to determine a plane of motion of the head (i.e., directionality), and a fourth sensor to determine the velocity and magnitude of the peak pressure. In one aspect, the positive-pressure-change gauges responds only to positive pressure above a certain threshold pressure. In another aspect, the threshold pressure may be chosen to neglect pressure changes due to weather or altitude.

Figure 4:
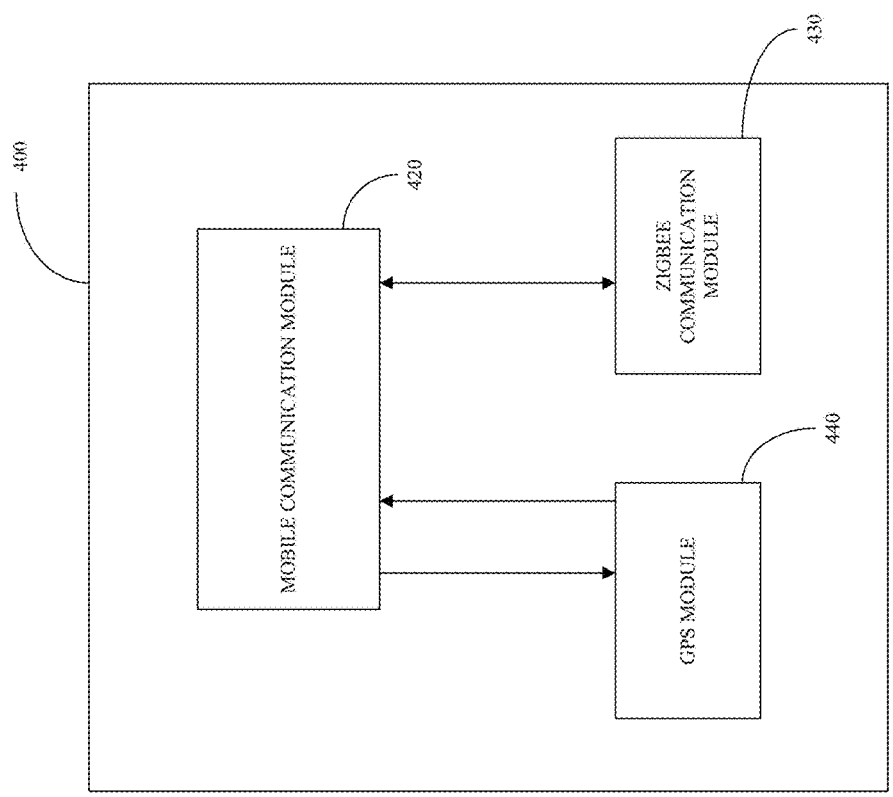
FIG. 4 is a simplified schematic illustrating a mobile device according to exemplary embodiments.

Referring to FIG. 4, there is shown a schematic diagram of a mobile device 400 which is particularly suited for combining the transceiver and first processor functions. The mobile device 400 includes a ZigBee communication module 430 for executing a ZigBee communication according to IEEE 802.15.4 standards, a global positioning system (GPS) module 440 obtaining the position data of the mobile device, and a mobile communication module 420 for communicating on the wireless network. In a preferred aspect, the ZigBee communication protocol is particularly suited for use with low-power sensors.

ZigBee wireless network communication protocol suite is based on the IEEE 802.15.4 standard and typically operates at the globally available 2.4 GHz bandwidth and provide a data rate of 250 Kbits/second. ZigBee is a low-cost, low-power, wireless mesh networking standard which affords a number of advantages. The low cost allows the technology to be widely deployed in wireless control and monitoring applications. Further, the low power-usage allows longer life with smaller batteries. Additionally, the mesh networking provides high reliability and more extensive range.

The ZigBee communication module interacts with the GPS module. The GPS module generates GPS reference signals, and a GPS module embedded in each mobile device for receiving and processing these GPS reference signals.

Referring back to FIG. 2, the second mobile device 260 runs System Device Software in accordance with aspects of the invention. In one aspect, the mobile device 220 also runs System Device Software in accordance with aspects of the invention so that the subject 250 can monitor the sensor data. In another aspect, the second mobile device 260 controls the user interface of the mobile device 220 to allow a parent or caregiver to interact with the sensor data. The second mobile device 260 or the mobile device 220 uses device drivers and display drivers to communicate with the display screen.

In a preferred aspect, a shell program executes at the highest level of the processor. The shell program may be implemented using, for example, native code, JAVA, JAVASCRIPT, ActiveX controls, HTML, and/or dynamic link libraries (DLLs). The shell program is the controlling application and provides the user interface (UI) on the mobile device 220 or the second mobile device 260 for telephone functionalities, electronic mail, text messaging, storing user preferences, and the like.

In a preferred aspect, the shell program contains a set of foundation layer APIs that can be called by programs downloaded via the data network. In one aspect, the functions in the APIs are accessed by JAVASCRIPT code downloaded to the client via HTTP. All functions available through the APIs are subject to access control and a program making use of the APIs must be authorized to access the functions.

Some examples of the sets of exemplary sets of APIs are described below. As described therein, the APIs allow a mobile device to run "applets" or "widgets" for various functionalities. These applets allow the mobile device to have extended functionalities so that the mobile device may be used for entertainment, navigation, personal information management, web browsing, news reading, camera functions, and the like. Various user interface elements may also be manipulated by the APIs so that retrieved information may be displayed to the user in various ways.

Additional APIs may allow accessing the sensor data so that JAVASCRIPT programs may display the data to the subject patient in informational ways. The APIs allow certain programs to graphically display the sensor data in a graph on a time axis so that the user can determine the time varying characteristics of certain sensor data. For instance, in one aspect, a parent or caregiver may chart the acceleration forces on a child's (or another subject's) head over varying time axis. The sensor data may also be correlated to different aspects of the child's activities.

As a further example, the acceleration forces on a child's head may be correlated and grouped according to the various activities that the child may be engaged in. It is contemplated, for instance, that the acceleration forces on a child's head during the child's soccer activities may be compared to the acceleration forces on a child's head during the child's bicycle riding activities, and so forth. In another aspect, the APIs additionally allow certain programs or applets to overlay a particular axis of movement along the helmet sensor so that correlations and differentiations between disparate activities may be readily discerned.

Additional APIs allow for controlling the interrupt of the mobile device 220 or the second mobile device 260 so that if the acceleration forces on a child's head reaches a predetermined threshold, the parent or caregiver is immediately notified, irrespective of settings or current activities of the respective mobile devices 220 or 260. The immediate notification may be in the form of a chime, vibrating, constant buzzing, or graphical notification. It will be understood that numerous other APIs can easily be added to the shell to provide functionality desired by the service provider, the user, or the child. Additional APIs allow for a graphical user interface (GUI) so that an icon or graphic symbol can indicate the general well-being of the child. For instance, a smile icon may indicate the child's overall well-being or the number of days since the last head acceleration event.

The second mobile device 260 of the parent or caregiver may be selected to communicate with the communications network by way of Wi-Fi signals on wireless communications path. The data may be converted to the TCP/IP protocol and respectively transmitted from the mobile device through the data network for storage and later transmission. In another aspect, expediency is important in communicating with emergency services and rescue personnel.

The wireless communications path provides a gateway allowing communication between the cellular data network and the Internet so that the same TCP/IP communications among the mobile devices and the system server may occur. In some aspects, restricted communications are used to ensure the system is limited to certain participants. In other aspects, encrypted communications are used to ensure the security of transmitted data. In still other embodiments, standard device and communications security principles are applied to produce a secure system.

A further resource that may be availed of by the System Device Software residing on the mobile device is the geographic location system such as the Global Positioning System (GPS). Signals generated by GPS satellites are transmitted along wireless communications paths leading respectively to the mobile devices. From such signals, the System Device Software residing on the mobile devices are used to determine the geographic location of the user's mobile device as desired. Some mobile cellular phones provide other geographic location systems, such as a triangulation-of-position system that determines locations relative to cellular radio towers at known fixed locations, or systems that recognize the presence of unique short-range radio signals known to exist only in a given geographical location.

Figure 5:
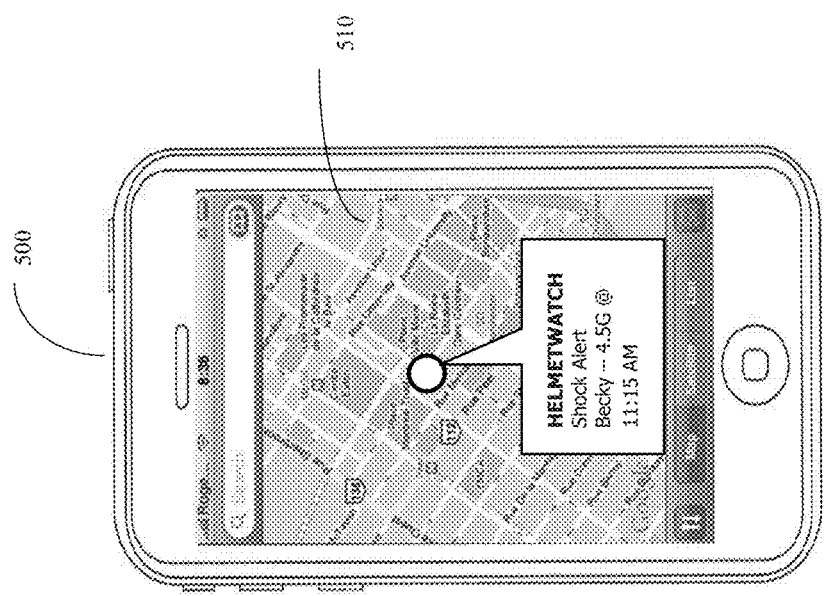
FIG. 5 is a simplified schematic illustrating an operating environment according to exemplary embodiments.

Referring to FIGS. 5-8, there are shown graphical representations of the user interface displayed by System Device Software to a user in the process of inputting preferences. FIG. 5, for example depicts an exemplary aspect of the user interface 510 on a mobile device 500 which displays a geographical map showing the incidence of a shock alert. In one aspect, when a child or user experiences an acceleration force to the head and the acceleration force exceeds a predetermined threshold the caregiver's mobile device is immediately notified of the incident. As shown, the incident is displayed on a graphical map showing the exact location and time of the incident. In one aspect, the incident is shown on the mobile device until the applet is manually dismissed or closed by the user. This ensures that the incident is a constant reminder to the parent or caregiver of an incident that needs to be resolved.

Depending on the user threshold level set for incident notification, an acceleration force incident may be configured by the user to interrupt the user at various levels of notification. For instance, the graphical representation of the incident may be accompanied by some combination of a vibration, buzzing, ringing, or chime from the mobile device, or some combination thereof. Of course, if the user has set a low threshold for acceleration force notification, the user may have the option to set a low interrupt notification level so that the user is not interrupted often. In another aspect, the user may have the option of setting a hybrid level of interruption so that relatively minor incidents of acceleration forces are merely logged, while major incidents of acceleration forces are accompanied by an associated level of interruption of the user.

Figure 6:
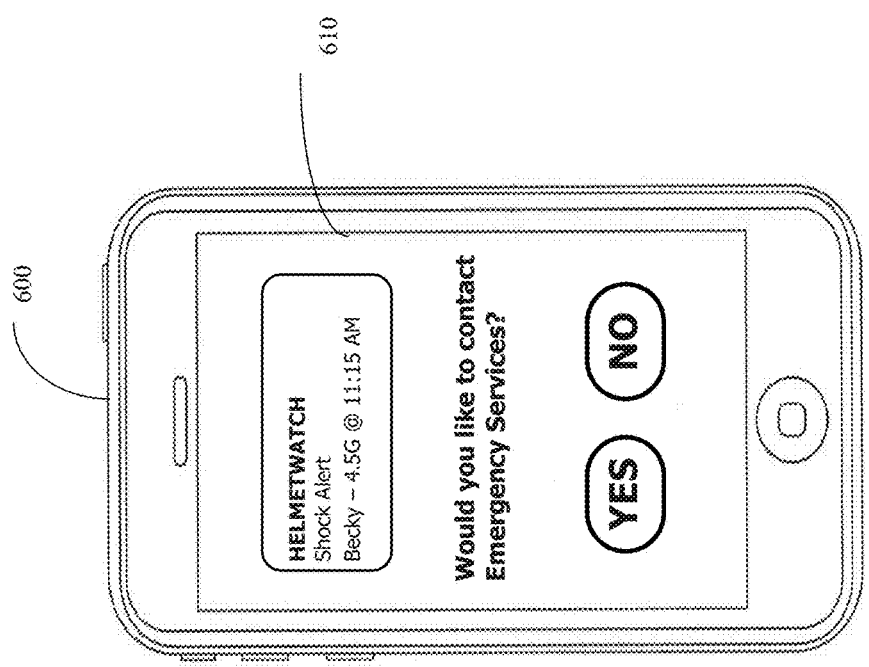
FIG. 6 is a simplified schematic illustrating a biometric sensor according to exemplary embodiments.
Figure 7:
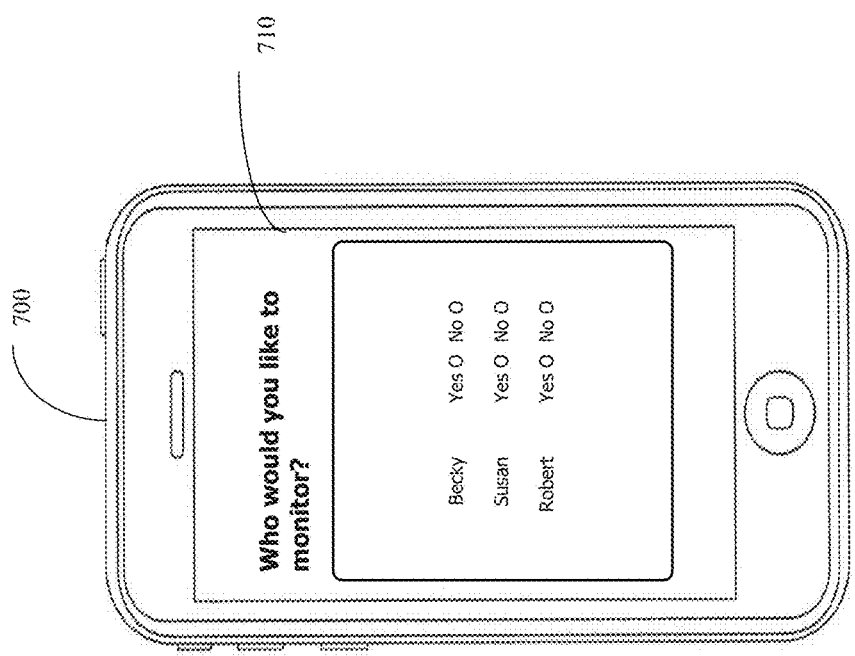
FIG. 7 is a simplified schematic illustrating a database engine according to exemplary embodiments.
Figure 8:
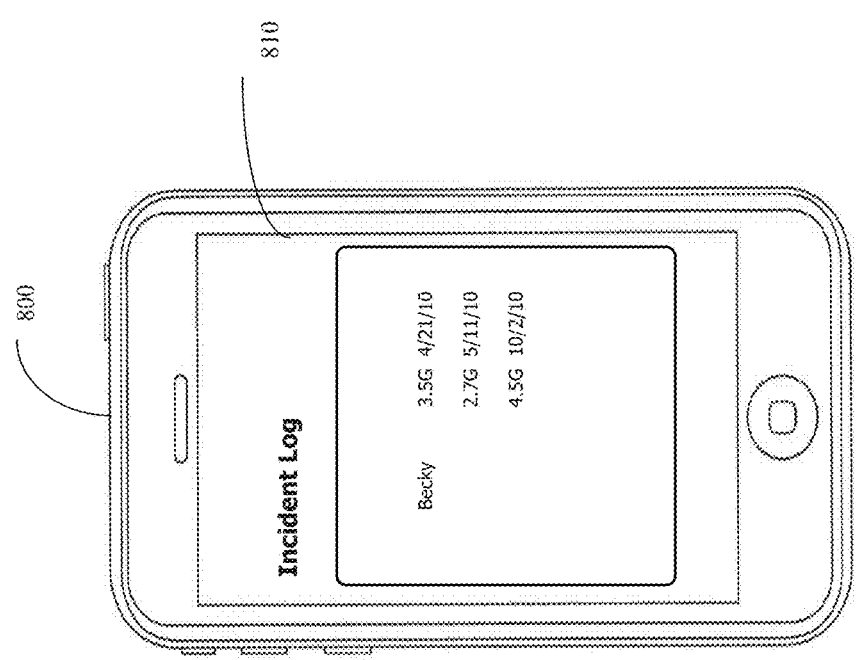
FIG. 8 is a simplified schematic illustrating a database engine according to exemplary embodiments.

FIG. 6 depicts an exemplary aspect of the user interface 610 on a mobile device 600 which displays an option to notify emergence services immediately from within the applet. The user is given the option to notify emergency services immediately, and if the user chooses the option to contact emergency services, the mobile device routes the call immediately. In another aspect, the E911 GPS coordinates for the incident are modified by the applet so that the location of the emergency call is relayed to emergency services as the location of the acceleration forces incident. FIG. 7 depicts an exemplary aspect of the user interface 710 on a mobile device 700 which displays, in tabular format, a list of children to monitor. The user is given the choice to monitor any of the children from within the applet or to monitor any other party or subject for which the user is authorized to monitor. FIG. 8 depicts an exemplary aspect of the user interface 810 on a mobile device 800 which displays an incident log. The user interface displays a log or archive of various acceleration forces incidents for each child.

Various other analyses and monitoring of the child's activities are contemplated. For example, the master agent may be able to comparatively log and analyze acceleration forces data against other children engaging in the same or similar type of activity. Custom Menu Interfaces allow a parent or caregiver to respond through the child's mobile device so that the parent may respond through video conferencing with the child. The menu may include interactive queries or solicit information regarding the child's daily goals, subjective opinions or overall impression of the activity and ones performance which could be incorporated in the Motivation Index described below.

Various other Report Generation Tools and Templates are also contemplated. XML, HTML or other authoring language used to create documents on the Web that would provide an interactive browser-based user interface to access additional performance data analysis and report generation tools and templates that may not be available or offered with the standard product.

A Custom Performance Algorithm can include a performance analysis which is specifically tailored to the child and the particular sport or activity. Certain application-specific performance analysis may require dynamically linked algorithms that process and calculate non-standard or specialized information, values, units, physical measurements, statistical results, predictive behaviors, filtering, numerical analysis including differentiation and integration, convolution and correlation, linear algebraic matrices operations to compute data pose and scaling transformation, and proprietary types. One example of a proprietary type is Motivation Index, a composite numerical value derived from a weighted average of statistical performance indicators and subjective user input including relative scoring improvements, conformity to ROM pattern, lengthy activity access duration, high access rate, relative skill level improvement, daily goal achievement, etc., that could represent the overall level of enthusiasm and satisfaction, the user has for a particular activity.

As a further example, a Range of Motion (RoM) Pattern Generator provides key control points to be captured along the desired trajectory and stored in order that the algorithm can calculate an optimally smooth path, in real-time, during the comparative analysis phase. A further example is a RoM Pattern Capture & Replay so that the athlete can replay the performance. The RoM pattern can be can saved to memory in real-time by discrete position samples versus time depending upon the resolution desired and memory limitations and later played back on the transponder or remote display for analysis.

It is contemplated that other Activity Specific Attributes, including Reps/Sets, Duration, Pause, Heart Rate Limits, intra-activity delay, level, point scalars, energy expenditure, task-oriented triggers, etc., and other parametric data that controls intensity, execution rate and scoring criteria for the activity may also be measured and analyzed.

Figure 9:
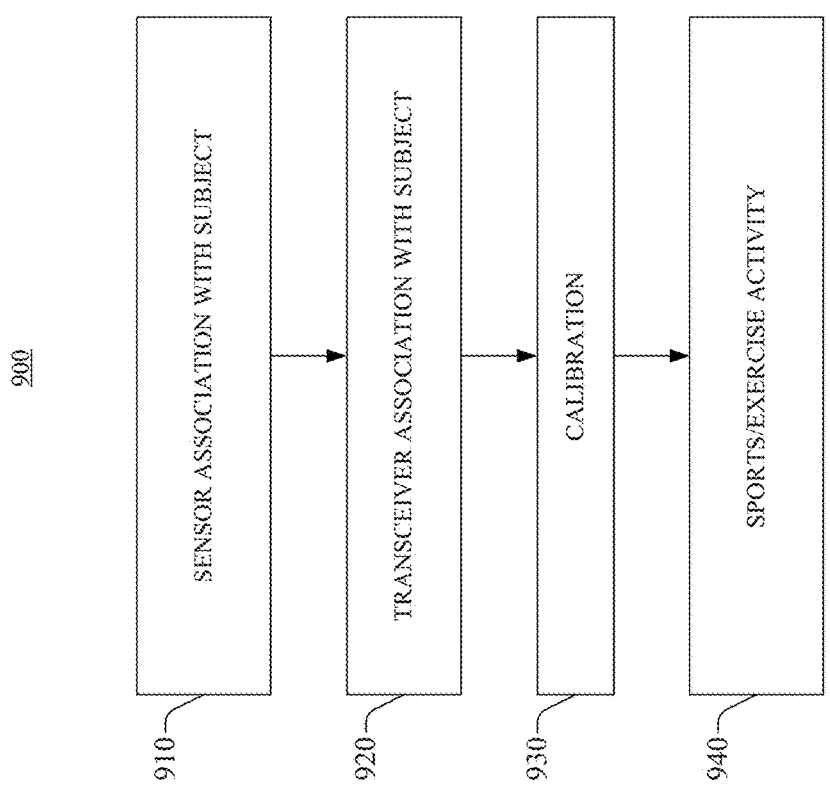
FIG. 9 is a flowchart illustrating the example steps according to exemplary embodiments.

FIG. 9 is a flowchart of an example method 900 for initializing the sensor arrangement at the commencement of a sports or athletic activity. At 910, the sensor is associated with the subject, in most cases a child. In one aspect, the step can include the authenticating of various sensors (mating of a sensor with a transceiver) so that sensors transmit data to the appropriate transceiver. In one aspect, for a transceiver utilizing the ZigBee communication protocol, the sensors must be mated to the ZigBee controller. At 920, the transceiver is authenticated with a particular subject. In one aspect, the association with a particular user includes mediating user rights at a login session, authenticate user name and password, and to manage session tokens. At 930, the sensors are calibrated for proper performance. At 940, the subject may begin any sports or exercise activity.

Figure 10:
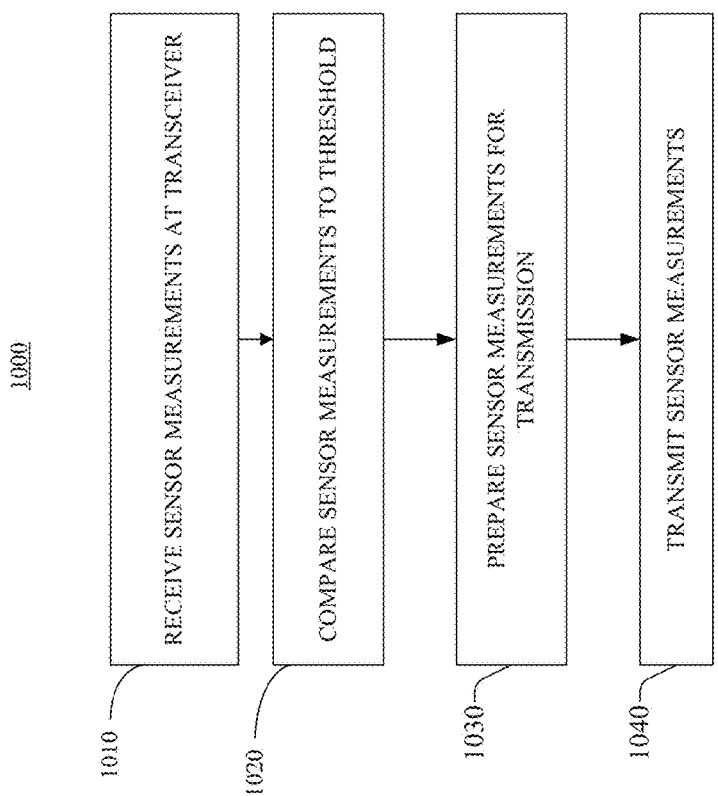
FIG. 10 is a flowchart illustrating the example steps according to exemplary embodiments.

FIG. 10 is a flowchart example of a method 1000 for transceiver data transmission. At 1010, the transceiver receives sensor measurements. At 1020, the sensor measurements are compared to a threshold level for incident reporting. The threshold may be user configurable so that only incidents above a certain number of Gs of acceleration are transmitted. At 1030, the transceiver prepares the sensor measurements for transmission. The transceiver can collect and store data (e.g., analog and/or digital data) from the sensors. In one aspect, the data is converted from analog to digital in the sensors or the transceiver to facilitate storage and/or transmittance. In another aspect, the data is sequenced, coded, and or separated to make the reception, storage, and/or transmission more efficient. At 1040, the further processed sensor data is transmitted.

Figure 11:
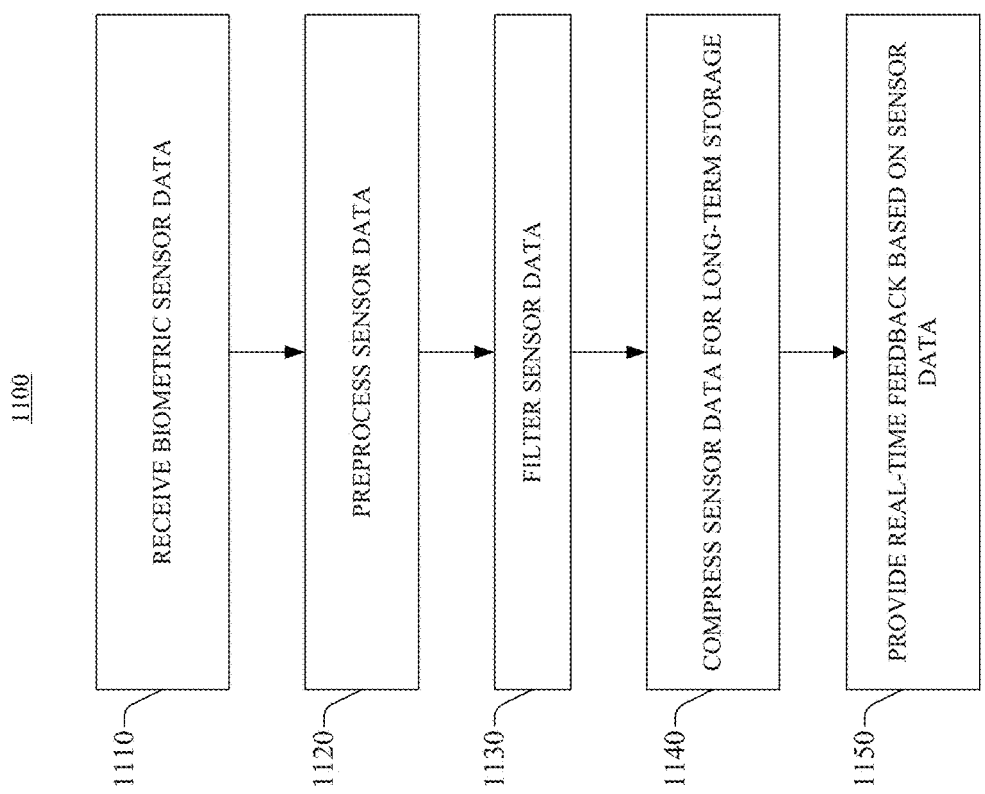
FIG. 11 is a flowchart illustrating the example steps according to exemplary embodiments.

FIG. 11 is a flowchart example of a method 1100 for receiving and analyzing sensor data at the database engine. At 1110, the database engine receives biometric sensor data. At 1120, the preprocessor receives the sensor data so that various noises are removed from the data resulting in a data with a higher signal to noise ratio. In one aspect, the preprocessor extracts identifiable features from the data so that windowing, sub-band transformation, mean extraction, and re-sampling may be prioritized in the extraction of data from the signal.

At 1130, the real-time filter extracts or filters out data that may be necessary for archival or historical purposes from the necessary data for real-time analysis. In one aspect, the filter produces a result, typically based on the entire record, based on access records which are typically not applied in a child's sports or exercise activity. The real-time filter applies access rules so that unauthorized data is not accessible to inappropriate personnel. In another aspect, the filter applies rule validation and administration for firewalls. Filter rules on a firewall between a secure computer network and a nonsecure computer network are validated from a user interface.

A user interface is presented in which a test packet can be defined. The user interface includes controls for defining values for attributes of the test packet, wherein the attributes of the test packet are selected from a set of attributes of normal packets normally sent between the secure and non-secure computer networks. A defined test packet is validated against a set of filter rules in the firewall or matched against the filter rules to determine those filter rules with matching attributes to the defined packet. When validating, responsive to the failure of the test packet in the validating step, the filter rule in the set of filter rules that denied the test packet is displayed. The results must then be filtered based on the defined rules.

At 1140, the compression module compresses sensor data for long-term storage. The compression module, in one aspect, applies an efficient data compression/decompression scheme using a passive data storage media for storage of athletic performance information. The system operates on central processing hardware so that efficient storage and retrieval of information may be provided.

At 1150, the master agent provides feedback to the athlete and acts as a "virtual" trainer or coach. In the absence of a human coach or trainer (or as a supplement thereto), the master agent analyzes the data instantaneously and provides statistical analysis and real-time feedback to the athlete. For example, the master agent collects data from multiple subjects or multiple users and processes that data to find patterns or establish norms. In some aspects, the master agent can include rules based analysis so that an individual training program is analyzed and compared to an exercise program to a previously stored reference workout or other benchmark.

As a further example, the master agent can monitor an athlete workout in real time by monitoring sensor data captured and wirelessly transmitted to the trainer display system. As used herein, the term "real time" is used broadly to mean that the data is not available hours later, but is instead available within less than one hour. In a preferred aspect, the monitoring and some analysis can be done substantially instantaneously. Advantageously, high-speed data transfer can allow monitoring to occur within a short time (e.g., less than 5 minutes) of the body movement. In some aspects, monitoring can occur within less than one minute of the body movement.

Figure 12:
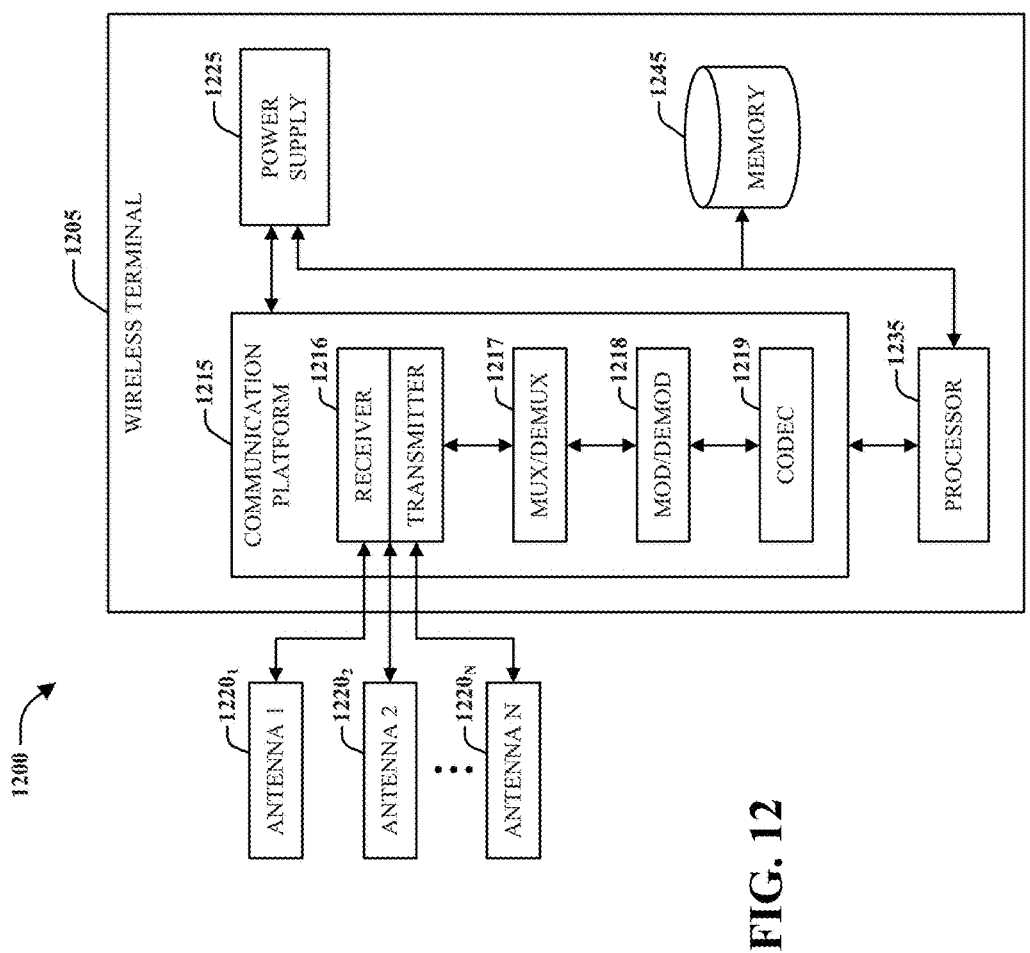
FIG. 12 illustrates an example network device that can be utilized to implement one or more of the various aspects described herein.

In one aspect, all data is stored so that analysis of that data can be compared to other athletes and enhance the training programs. In order to provide further context for various aspects of the disclosed subject matter, FIG. 12 illustrates a non-limiting example system 1200 that can implement some or all of the aspects described herein. As FIG. 12 illustrates, system 1200 can include a wireless terminal 1205. In an embodiment, wireless terminal 1205 can receive and transmit signal(s) to and/or from wireless devices such as femto access points, access terminals, wireless ports and routers, or the like, through a set of N antennas 1220. In one example, antennas 1220 can be implemented as part of a communication platform 1215, which in turn can comprise electronic components and associated circuitry and/or other means that provide for processing and manipulation of received signal(s) and signal(s) to be transmitted.

In an aspect, communication platform 1215 can include a receiver/transmitter or transceiver 1216, which can transmit and receive signals and/or perform one or more processing operations on such signals (e.g., conversion from analog to digital upon reception, conversion from digital to analog upon transmission, etc.). In addition, transceiver 1216 can divide a single data stream into multiple, parallel data streams, or perform the reciprocal operation.

In another example, a multiplexer/demultiplexer (mux/demux) unit 1217 can be coupled to transceiver 1216. Mux/demux unit 1217 can, for example, facilitate manipulation of signal in time and frequency space. Additionally or alternatively, mux/demux unit 1217 can multiplex information (e.g., data/traffic, control/signaling, etc.) according to various multiplexing schemes such as time division multiplexing (TDM), frequency division multiplexing (FDM), orthogonal frequency division multiplexing (OFDM), code division multiplexing (CDM), space division multiplexing (SDM), or the like. In addition, mux/demux unit 1217 can scramble and spread information according to substantially any code generally known in the art, such as Hadamard-Walsh codes, Baker codes, Kasami codes, polyphase codes, and so on.

In a further example, a modulator/demodulator (mod/demod) unit 1218 implemented within communication platform 1215 can modulate information according to multiple modulation techniques, such as frequency modulation, amplitude modulation (e.g., N-ary quadrature amplitude modulation (N-QAM), etc.), phase-shift keying (PSK), and the like. Further, communication platform 1215 can also include a coder/decoder (codec) module 1219 that facilitates decoding received signal(s) and/or coding signal(s) to convey.

According to another aspect, wireless terminal 1205 can include a processor 1235 configured to confer functionality, at least in part, to substantially any electronic component utilized by wireless terminal 1205. As further shown in system 1200, a power supply 1225 can attach to a power grid and include one or more transformers to achieve a power level at which various components and/or circuitry associated with wireless terminal 1205 can operate. In one example, power supply 1225 can include a rechargeable power mechanism to facilitate continued operation of wireless terminal 1205 in the event that wireless terminal 1205 is disconnected from the power grid, the power grid is not operating, etc.

In a further aspect, processor 1235 can be functionally connected to communication platform 1215 and can facilitate various operations on data (e.g., symbols, bits, chips, etc.), which can include, but are not limited to, effecting direct and inverse fast Fourier transforms, selection of modulation rates, selection of data packet formats, inter-packet times, etc. In another example, processor 1235 can be functionally connected, via a data or system bus, to any other components or circuitry not shown in system 1200 to at least partially confer functionality to each of such components.

As additionally illustrated in system 1200, a memory 1245 can be used by wireless terminal 1205 to store data structures, code instructions and program modules, system or device information, code sequences for scrambling, spreading and pilot transmission, location intelligence storage, determined delay offset(s), over-the-air propagation models, and so on. Processor 1235 can be coupled to the memory 1245 in order to store and retrieve information necessary to operate and/or confer functionality to communication platform 1215 and/or any other components of wireless terminal 1205.

Figure 13:
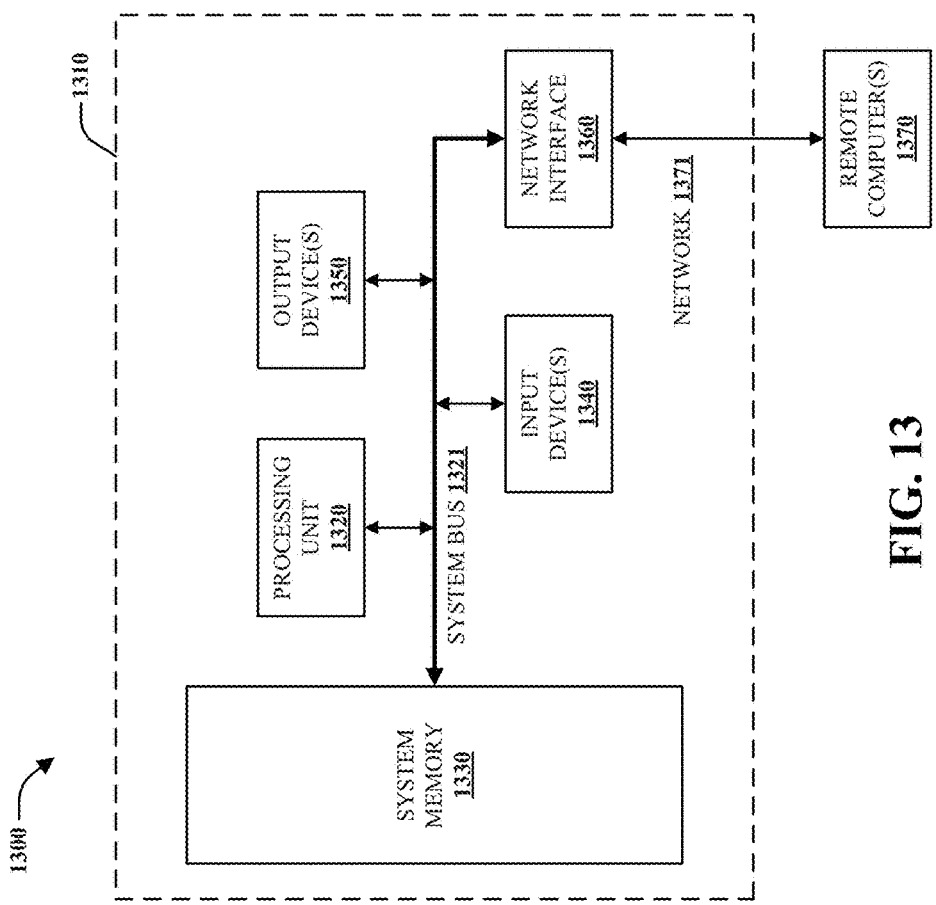
FIG. 13 illustrates an example computing architecture that is operable to execute various aspects described herein.

Turning to FIG. 13, a non-limiting example computing system or operating environment in which various aspects of the disclosed subject matter may be implemented is illustrated. One of ordinary skill in the art can appreciate that handheld, portable and other computing devices and computing objects of all kinds are contemplated for use in connection with the disclosed subject matter, e.g., anywhere that a communications system may be desirably configured. Accordingly, the below general purpose remote computer described below in FIG. 13 is but one example of a computing system in which the disclosed subject matter may be implemented.

Although not required, various aspects of the disclosed subject matter can partly be implemented via an operating system, for use by a developer of services for a device or object, and/or included within application software that operates in connection with the component(s) of the disclosed subject matter. Software may be described in the general context of computer-executable instructions, such as program modules, being executed by one or more computers, such as client workstations, servers or other devices. Those skilled in the art will appreciate that various aspects of the disclosed subject matter may be practiced with other computer system configurations and protocols.

FIG. 13 thus illustrates an example of a suitable computing system environment 1300 in which various aspects of the disclosed subject matter may be implemented, although as made clear above, the computing system environment 1300 is only one example of a suitable computing environment for a media device and is not intended to suggest any limitation as to the scope of use or functionality of the disclosed subject matter. Neither should the computing environment 1300 be interpreted as having any dependency or requirement relating to any one or combination of components illustrated in the example operating environment 1300.

With reference to FIG. 13, an example of a computing environment 1300 for implementing various aspects of the disclosed subject matter includes a general purpose computing device in the form of a computer 1310. Components of computer 1310 can include, but are not limited to, a processing unit 1320, a system memory 1330, and a system bus 1321 that couples various system components including the system memory to the processing unit 1320. The system bus 1321 can be any of several types of bus structures including a memory bus or memory controller, a peripheral bus, and a local bus using any of a variety of bus architectures.

Computer 1310 can include a variety of media, which can include computer-readable storage media and/or communications media, which two terms are used herein differently from one another as follows. Computer-readable storage media can be any available storage media that can be accessed by the computer and includes both volatile and nonvolatile media, removable and non-removable media. By way of example, and not limitation, computer-readable storage media can be implemented in connection with any method or technology for storage of information such as computer-readable instructions, program modules, structured data, or unstructured data. Computer-readable storage media can include, but are not limited to, RAM, ROM, Electrically Erasable Programmable ROM (EEPROM), flash memory or other memory technology, CD-ROM, digital versatile disk (DVD) or other optical disk storage, magnetic cassettes, magnetic tape, magnetic disk storage or other magnetic storage devices, or other tangible and/or non-transitory media which can be used to store desired information. Computer-readable storage media can be accessed by one or more local or remote computing devices, e.g., via access requests, queries or other data retrieval protocols, for a variety of operations with respect to the information stored by the medium.

Communications media typically embody computer-readable instructions, data structures, program modules or other structured or unstructured data in a data signal such as a modulated data signal, e.g., a carrier wave or other transport mechanism, and include any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

The system memory 1330 can include computer storage media in the form of volatile and/or nonvolatile memory such as read only memory (ROM) and/or random access memory (RAM). A basic input/output system (BIOS), containing the basic routines that help to transfer information between elements within computer 1310, such as during start-up, can be stored in memory 1330. Memory 1330 typically also contains data and/or program modules that are immediately accessible to and/or presently being operated on by processing unit 1320. By way of example, and not limitation, memory 1330 can also include an operating system, application programs, other program modules, and program data.

The computer 1310 can also include other removable/non-removable, volatile/nonvolatile computer storage media. For example, computer 1310 could include a hard disk drive that reads from or writes to non-removable, nonvolatile magnetic media, a magnetic disk drive that reads from or writes to a removable, nonvolatile magnetic disk, and/or an optical disk drive that reads from or writes to a removable, nonvolatile optical disk, such as a CD-ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM and the like. A hard disk drive is typically connected to the system bus 1321 through a non-removable memory interface such as an interface, and a magnetic disk drive or optical disk drive is typically connected to the system bus 1321 by a removable memory interface, such as an interface.

A user can enter commands and information into the computer 1310 through input devices such as a keyboard and pointing device, commonly referred to as a mouse, trackball or touch pad. Other input devices can include a microphone, joystick, game pad, satellite dish, scanner, or the like. These and other input devices are often connected to the processing unit 1320 through user input 1340 and associated interface(s) that are coupled to the system bus 1321, but can be connected by other interface and bus structures, such as a parallel port, game port or a universal serial bus (USB). A graphics subsystem can also be connected to the system bus 1321. A monitor or other type of display device is also connected to the system bus 1321 via an interface, such as output interface 1350, which can in turn communicate with video memory. In addition to a monitor, computers can also include other peripheral output devices such as speakers and a printer, which can be connected through output interface 1350.

The computer 1310 can operate in a networked or distributed environment using logical connections to one or more other remote computers, such as remote computer 1370, which can in turn have media capabilities different from device 1310. The remote computer 1370 can be a personal computer, a server, a router, a network PC, a peer device or other common network node, or any other remote media consumption or transmission device, and can include any or all of the elements described above relative to the computer 1310. The logical connections depicted in FIG. 13 include a network 1371, such local area network (LAN) or a wide area network (WAN), but can also include other networks/buses. Such networking environments are commonplace in homes, offices, enterprise-wide computer networks, intranets and the Internet.

When used in a LAN networking environment, the computer 1310 is connected to the LAN 1371 through a network interface or adapter. When used in a WAN networking environment, the computer 1310 typically includes a communications component, such as a modem, or other means for establishing communications over the WAN, such as the Internet. A communications component, such as a modem, which can be internal or external, can be connected to the system bus 1321 via the user input interface of input 1340, or other appropriate mechanism. In a networked environment, program modules depicted relative to the computer 1310, or portions thereof, can be stored in a remote memory storage device. It will be appreciated that the network connections shown and described are exemplary and other means of establishing a communications link between the computers can be used.

It is to be noted that aspects, features, and/or advantages of the disclosed subject matter can be exploited in substantially any wireless telecommunication or radio technology, e.g., Wi-Fi; Bluetooth; Worldwide Interoperability for Microwave Access (WiMAX); Enhanced General Packet Radio Service (Enhanced GPRS); Third Generation Partnership Project (3GPP) Long Term Evolution (LTE); Third Generation Partnership Project 2 (3GPP2) Ultra Mobile Broadband (UMB); 3GPP Universal Mobile Telecommunication System (UMTS); High Speed Packet Access (HSPA); High Speed Downlink Packet Access (HSDPA); High Speed Uplink Packet Access (HSUPA); GSM (Global System for Mobile Communications) EDGE (Enhanced Data Rates for GSM Evolution) Radio Access Network (GERAN); UMTS Terrestrial Radio Access Network (UTRAN); LTE Advanced (LTE-A); etc. Additionally, some or all of the aspects described herein can be exploited in legacy telecommunication technologies, e.g., GSM. In addition, mobile as well non-mobile networks (e.g., the Internet, data service network such as internet protocol television (IPTV), etc.) can exploit aspects or features described herein.

Various aspects or features described herein can be implemented as a method, apparatus, system, or article of manufacture using standard programming or engineering techniques. In addition, various aspects or features disclosed in the subject specification can also be realized through program modules that implement at least one or more of the methods disclosed herein, the program modules being stored in a memory and executed by at least a processor. Other combinations of hardware and software or hardware and firmware can enable or implement aspects described herein, including disclosed method(s).

Computing devices typically include a variety of media, which can include computer-readable storage media or communications media, which two terms are used herein differently from one another as follows. Computer-readable storage media can be any available storage media that can be accessed by the computer and includes both volatile and nonvolatile media, removable and non-removable media. By way of example, and not limitation, computer-readable storage media can be implemented in connection with any method or technology for storage of information such as computer-readable instructions, program modules, structured data, or unstructured data. Computer-readable storage media can include, but are not limited to, RAM, ROM, EEPROM, flash memory or other memory technology, CD-ROM, digital versatile disk (DVD) or other optical disk storage, magnetic cassettes, magnetic tape, magnetic disk storage or other magnetic storage devices, or other tangible and/or non-transitory media which can be used to store desired information. Computer-readable storage media can be accessed by one or more local or remote computing devices, e.g., via access requests, queries or other data retrieval protocols, for a variety of operations with respect to the information stored by the medium.

Communications media typically embody computer-readable instructions, data structures, program modules or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor may also be implemented as a combination of computing processing units.

In the subject specification, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory.

By way of illustration, and not limitation, nonvolatile memory can include read only memory (ROM), programmable ROM (PROM), electrically programmable ROM (EPROM), electrically erasable ROM (EEPROM), or flash memory. Volatile memory can include random access memory (RAM), which acts as external cache memory. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM). Additionally, the disclosed memory components of systems or methods herein are intended to comprise, without being limited to comprising, these and any other suitable types of memory.

What has been described above includes examples of systems and methods that provide advantages of the disclosed subject matter. It is, of course, not possible to describe every conceivable combination of components or methodologies for purposes of describing the disclosed subject matter, but one of ordinary skill in the art may recognize that many further combinations and permutations of the claimed subject matter are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

What is claimed is:

1. A system, comprising:
   a processor; and
   a memory that stores executable instructions that, when executed by the processor, facilitate performance of operations, comprising:
   receiving, from a wireless transceiver of a helmet corresponding to a head of a person, first pressure data representing a first pressure that has been applied to the head during a first type of activity determined to be performed by the person; and
   displaying the first pressure data representing the first pressure that has been applied to the head during the first type of activity with second pressure data representing a second pressure that has been applied to the head during a second type of activity determined to be performed by the person that is different from the first type of activity.

2. The system of claim 1, wherein the operations further comprise:
   determining whether head acceleration force data associated with movements of the head during the first type of activity satisfies a defined condition related to a head injury.

3. The system of claim 2, wherein the operations further comprise:
   in response to determining that the head acceleration force data satisfies the defined condition, sending the first pressure data directed to a device.

4. The system of claim 1, wherein the operations further comprise:
   correlating head acceleration force data associated with movements of the head with the first type of activity and the second type of activity.

5. The system of claim 4, wherein the operations further comprises:
   in response to the correlating, displaying respective axes of movement of respective uses associated with the first type of activity and the second type of activity.

6. The system of claim 1, wherein the operations further comprise:
   determining an acceleration of the head; and
   determining a period of time since the acceleration.

7. The system of claim 6, wherein the operations further comprise:
   displaying a symbol corresponding to the period of time.

8. The system of claim 1, further comprising an array of sensors, wherein the receiving further comprises:
   obtaining the first pressure data via the wireless transceiver from the array of sensors.

9. The system of claim 8, wherein the array of sensors comprises a microelectromechanical system accelerometer.

10. The system of claim 1, wherein the receiving comprises:
    receiving the first pressure data from the wireless transceiver utilizing a wireless communication protocol based on an Institute for Electronics Engineers 802.15.4 physical radio specification.

11. A method, comprising:
    receiving, by a system comprising a processor, pressure data from a transceiver coupled to a pressure sensitive sensor of a helmet, wherein the pressure data represents a first pressure applied to a portion of a head engaged in a first type of activity; and
    displaying the first pressure data representing the first pressure applied to the portion of the head with second pressure data representing a second pressure applied to the portion of the head engaged in a second type of activity that is different from the first type of activity.

12. The method of claim 11, further comprising:
    determining, by the system, whether an acceleration of the head satisfies a defined condition with respect to an anticipated injury of the head.

13. The method of claim 12, further comprising:
in response to determining that the acceleration satisfies the defined condition, sending, by the system, the first pressure data directed to a device.

14. The method of claim 11, further comprising:
comparing, by the system, head acceleration force data associated with movements of the head with different activities comprising the first type of activity and the second type of activity.

15. The method of claim 14, further comprising:
in response to the comparing, displaying, by the system, axes of the movements of the head.

16. The method of claim 11, further comprising:
determining, by the system, a acceleration of the head; and
determining, by the system, a period of time since the acceleration.

17. The method of claim 11, wherein the receiving comprises receiving the first pressure data via a ZigBee based wireless communication protocol.

18. A mobile device, comprising:
a processor; and
a memory that stores executable instructions that, when executed by the processor, facilitate performance of operations, comprising:
receiving pressure data from a wireless transceiver coupled to a pressure sensor of a helmet, wherein the pressure data represents respective pressures that have been determined to have been applied to a head of a person; and
displaying information presenting a first pressure of the respective pressures determined to have been applied to the head of the person during a first activity and a second pressure of the respective pressures determined to have been applied to the head of the person during a second activity different from the first activity.

19. The mobile device of claim 18, wherein the operations further comprise:
determining an acceleration of the head; and
in response to determining that the acceleration satisfies a defined condition with respect to a future injury of the head determined to be likely to occur, sending a message directed to a device.

20. The mobile device of claim 18, wherein the receiving comprises receiving the pressure data according to a ZigBee based communication protocol.

* * * * *